United States Patent
Heng

(10) Patent No.: US 6,593,118 B2
(45) Date of Patent: *Jul. 15, 2003

(54) METHOD FOR RAPIDLY OBTAINING CRYSTALS WITH DESIRABLE MORPHOLOGIES

(75) Inventor: Meng H. Heng, Belmont, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/053,199

(22) Filed: Nov. 2, 2001

(65) Prior Publication Data

US 2002/0177206 A1 Nov. 28, 2002

Related U.S. Application Data

(62) Division of application No. 09/518,786, filed on Mar. 3, 2000, now Pat. No. 6,403,350.
(60) Provisional application No. 60/123,147, filed on Mar. 5, 1999.

(51) Int. Cl.[7] .......................... C12N 9/100; C12N 9/02; C12N 9/04; C12N 9/10; C12N 9/26
(52) U.S. Cl. ..................... 435/183; 435/195; 435/219; 435/189; 435/190; 435/201; 435/209; 435/816; 435/814; 435/193
(58) Field of Search .................. 435/183, 195, 435/219, 189, 190, 201, 209, 816, 814, 193

(56) References Cited

U.S. PATENT DOCUMENTS

| 4,659,667 A | 4/1987 | Brewer et al. |
| 5,602,232 A | 2/1997 | Reichert et al. |

FOREIGN PATENT DOCUMENTS

| EP | 506866 | 10/1993 |
| WO | WO 89/08703 | 9/1989 |
| WO | WO 91/09943 | * 7/1991 |
| WO | WO 97/15660 | 5/1997 |
| WO | WO 97/33983 | 9/1997 |

OTHER PUBLICATIONS

Copy of International Search Report for PCT/US00/05564.

* cited by examiner

Primary Examiner—Michael V. Meller
(74) Attorney, Agent, or Firm—Genencor International Inc.

(57) ABSTRACT

The present invention provides a crystallization process wherein a starting temperature is selected such that a desirable crystal morphology (e.g., square) is obtained. A temperature shift is then introduced, providing that the shift is not enough to induce further nucleation, where the crystals continue to grow in the desirable fashion, but with different kinetics, e.g., a higher rate of crystallization. As a result, the process gives a crystalline product with desirable morphology at a higher crystallization rate.

14 Claims, 2 Drawing Sheets

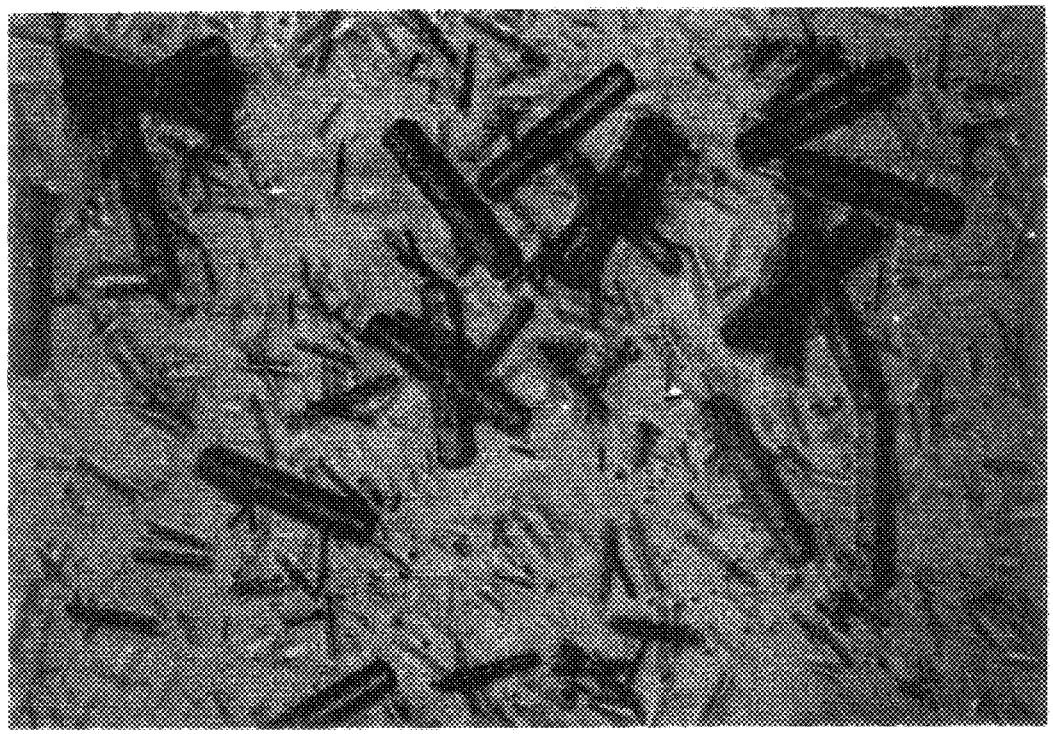
FIG._1
FIG._2

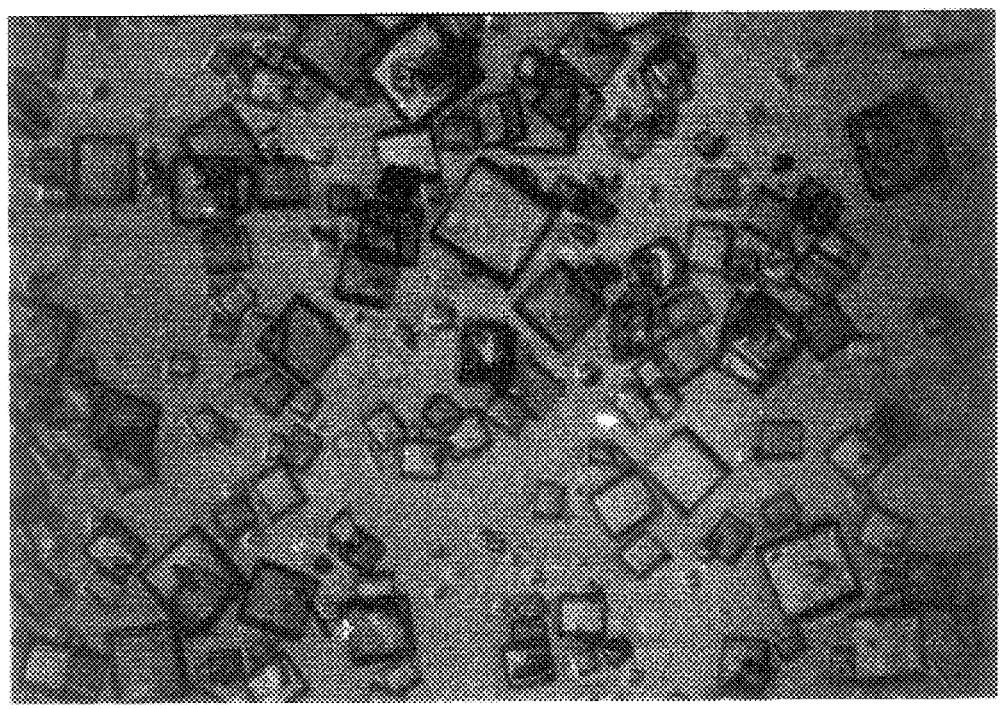
FIG. 3
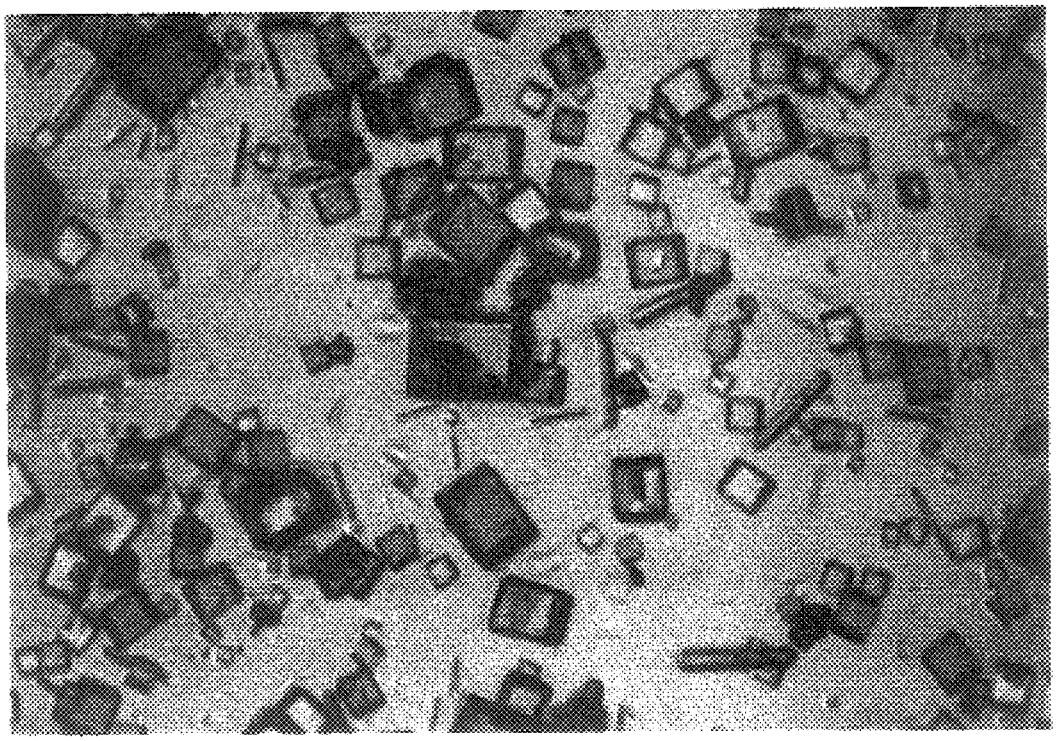
FIG._4

METHOD FOR RAPIDLY OBTAINING CRYSTALS WITH DESIRABLE MORPHOLOGIES

RELATED APPLICATION

This is a divisional of application Ser. No. 09/518,786, filed Mar. 3, 2000 now U.S. Pat. No. 6,403,350.

The present application claims priority to U.S. Provisional Application No. 60/123,147, filed Mar. 5, 1999, all of which is hereby incorporated herein in its entirety.

FIELD OF INVENTION

The present invention relates to crystallization, and particularly to a method for obtaining protein crystals having a desired morphology.

BACKGROUND OF THE INVENTION

Intensive research efforts have been directed to the precipitation and crystallization of enzyme as a means of purification and preparation of enzyme products. For example, in U.S. Pat. No. 4,654,667, a process is disclosed for the recovery of an enzyme from solution by concentrating to supersaturation the enzyme-containing solution at pH near the isoelectric point of the enzyme, inducing crystallization and recovering the crystallized final product. Inducing crystallization is achieved by allowing the enzymes to spontaneously crystallize upon concentration or by seeding, sound, stirring or scratching the inner surface of the container. Crystallization of alpha-amylase is exemplified.

In PCT Publication No. WO 89/08703, a process is described for the crystallization of subtilisin by adding a halide salt, such as sodium chloride or calcium chloride, to a concentrated subtilisin solution of at least about 40 grams per liter.

In EP 506,866, a method for the crystallization of enzymes is disclosed which is characterized by using as a starting material an aqueous solution containing liquid with a relatively high enzyme purity and a concentration of enzyme of about at least 5 grams per liter and adding as a crystallization agent an easily soluble salt of the non-halide type to a concentration which is considerably smaller than the amount necessary to precipitate the enzymes in an amorphous form. Crystallization of certain subtilisin enzymes at temperatures up to 30° C. is exemplified. Sodium sulfate is used to help purify the protease product but not for crystallization.

In spite of these advances in the field of enzyme crystallization, inexpensive and efficient crystallization of proteases suitable for large scale production has remained problematic in industry. The ability to rapidly produce crystals with a desirable morphology at an industrial scale would represent a large savings and be of great importance to the industry.

SUMMARY OF THE INVENTION

One aspect of the present invention provides a crystallization process for rapidly obtaining crystals having a desired morphology (e.g., square plates, hexagonal or rectangular crystals, etc.). Typically, the desired morphology will be one wherein the crystals exhibit increased strength over other possible crystal morphologies (e.g., square or rectangular plates or cubes, as opposed to elongated needles or rods). In one embodiment, a starting temperature is selected such that square-plate crystals are obtained. The starting temperature can be, for example, a temperature below room temperature (e.g., less than 20 degrees C.). A temperature shift or increase is then effected, preferably in a manner to minimize or avoid further nucleation, such that the crystals continue to grow on the square plates but with different kinetics, e.g., a higher rate of crystallization. The temperature shift can be, for example, to at least room temperature (e.g., between about 20 and 60 degrees C.). As a result, the process gives a crystalline product with the desirable morphology at a higher crystallization rate.

The method of the present invention is especially useful in quickly obtaining crystals of a protein, such as an enzyme, having a desired morphology. In one embodiment, the method is used to realize at least about 90% crystallization in less than 25 hours from a enzyme-containing solution, with the enzyme crystals having a predominantly square-plate morphology.

Other features, aspects and advantages of the present invention will become apparent from the following detailed description, in conjunction with the drawings and appended claims.

BRIEF DESCRIPTION OF THE DRAWINGS

FIG. 1 is a micrograph showing protease crystals obtained when crystallized from a solution maintained at about room temperature (22 degrees C.) over about 19.5 hours.

FIG. 2 is a micrograph showing protease crystals obtained when crystallized from a solution maintained at about 30 degrees C. over about 19.5 hours.

FIG. 3 is a micrograph showing protease crystals obtained when crystallized from a solution maintained at about 15 degrees C. over about 19.5 hours.

FIG. 4 is a micrograph showing protease crystals obtained according to the teachings of the present invention, wherein crystallization was allowed to begin at about 15 degrees C. for about 4 hours, and then continued after the temperature was shifted to about 22 degrees C. for an additional 18 hours. Note the substantial number of square-plate crystals.

DETAILED DESCRIPTION OF THE INVENTION

The present invention provides a crystallization process wherein a starting temperature is selected, e.g., below room temperature, such that a desirable crystal morphology (e.g., square plates) is obtained. A temperature shift is then introduced, e.g., to room temperature or above, where the crystals continue to grow in the desirable fashion, but with different kinetics, e.g., a higher rate of crystallization. As a result, the process gives a crystalline product with desirable morphology at a higher crystallization rate.

Once crystals exhibiting the desired morphology have begun to form at the starting temperature, an appropriate temperature shift can be selected that minimizes or eliminates further nucleation to thereby discourage the formation of crystals having a morphology other than that which is desired. For example, the temperature can be raised in discrete steps over a period time (e.g., in increments of about 4 degrees C., every 5 minutes, over a period of about 25 minutes). Or, a continuous ramping profile can be determined that minimizes further nucleation. Such a ramping profile can represent a steady rate increase, e.g., 2 degrees C./minute over a shift period of about 10 minutes, or the rate can vary over the shift period, e.g., 1 degree C./minute for 10 minutes, changing to 2 degrees C./minute for 5 minutes.

In recovering proteins using crystallization, there are a number of factors that must be balanced to arrive at crystals having a desired morphology including temperature, pH, salt used, amount of time for crystallization, morphology of the crystals.

Proteins that are within the scope of the present invention include pharmaceutically important proteins such as hormones or other therapeutic proteins and industrially important proteins such as enzymes.

Preferred enzymes include those enzymes capable of hydrolyzing substrates, e.g. stains. These enzymes are known as hydrolases which include, but are not limited to, proteases (bacterial, fungal, acid, neutral or alkaline), amylases (alpha or beta), lipases, cellulases and mixtures thereof. Particularly preferred enzymes are subtilisins and cellulases. Most preferred are subtilisins such as described in U.S. Pat. No. 4,760,025, EP Patent 130 756 B1 and EP Patent Application WO 91/06637, which are incorporated herein by reference. Other enzymes that can be used in the present invention include oxidases, transferases, dehydratases, reductases, hemicellulases and isomerases.

Genetically modified proteases which are derived from a DNA sequence in which one or more of the amino acids of the protease have been deleted, replaced or otherwise manipulated are also considered within the scope of the invention. Such modified proteases are described in, for example, PCT Publication No. WO 95/10615 and U.S. Pat. No. 5,185,258.

Preferably, enzymes recovered using the present crystallization process retain at least 80%, more preferably at least 90%, and most preferably at least 95%, of their original activity.

The fermentation procedures for culturing cells and for production of protein are known per se in the art. For example, protein can be produced either by solid or submerged culture, including batch, fed-batch and continuous-flow processes. The collection and purification of the protein from the fermentation broth can also be effected by procedures known per se in the art.

The aqueous solution which acts as starting material for the method according to the invention is derived from the fermentation broth produced by the fermentation of an appropriate microorganism. The fermentation broth will generally contain cellular debris including cells, various suspended solids and other biomass contaminants, as well as the desired protease product, which are preferably removed from the fermentation broth by means known in the art. Suitable processes for such removal include conventional solid-liquid separation techniques such as, e.g., centrifugation, filtration, dialysis, micro-filtration, rotary vacuum filtration, or other known processes, to produce a cell-free filtrate. While it is contemplated as within the scope of the invention to crystallize the protease enzyme either directly from the fermentation broth or from the cell-free filtrate, it is preferable to further concentrate the fermentation broth or the cell free filtrate prior to crystallization using techniques such as ultra-filtration, evaporation, or precipitation.

In the case of enzymes, it has long been known in the art that certain constituents, if included in a culture medium, will result in difficulty in crystallization of the component enzymes. For this reason, it is often advantageous to further purify the filtered fermentation broth to remove impurities which may interfere with crystallization by, for example, subjecting the filtered broth to column purification. Additionally, it is possible to limit the amount of such impurities by controlling the culture medium in which the microorganism is grown. For example, as described in Northrup et al. (1948) Crystalline Enzymes, Columbia University Press, p. 254, mucin-like substances, e.g., polysaccharides, are often detrimental to crystallization processes. Thus, by eliminating such polysaccharide components from the pre-fermentation culture medium or purifying such components from a fermentation broth, it is possible to improve the success of the subsequent crystallization. Alternatively, these substances can be removed by treatment of the filtrate with a strong acid, copper hydroxide, alcohol or acetone. Preferably, aluminum sulfate is used in purifying protease-containing fermentation broths in order to facilitate crystallization.

A number of different proteins exhibit different morphologies at different temperatures including enzymes such as certain proteases and glucose isomerases. Generally, the crystal morphology found at the lower temperature is the preferred. According to the present invention, this factor can be used to produce crystals with preferred crystal morphologies at a higher crystallization rate.

Preferred crystal morphologies are those which do not break easily when the crystals are being handled. Rods tend to break more easily than square, rectangular or hexagonal crystals.

The following examples are representative and not intended to be limiting.

EXAMPLES

Example 1

An aqueous solution comprising an ultra-filtrate concentrate of a fermentation broth of a mutant protease derived from the fermentation of *Bacillus subtilis* was prepared. Methods for preparing mutant protease suitable for the present purpose are described in U.S. Pat. No. 5,185,258. Ultra-filtration was carried out with a polysulfone membrane having a 10 kD molecular weight cut off in a spiral ultra-filtration unit. The resultant protease solution was at a concentration of about 52 g/l of active enzyme. The protease concentration can be determined by the method described in Estell et al. (1985) *J. Biol. Chem.* 260:6518–6521. This broth was used for all of the following crystallization experiments.

Crystallization of a Mutant Protease from Bacillus using Different Temperature Profiles Aqueous solutions comprising the ultra-filtrate concentrate of a fermentation broth of a mutant protease derived from *Bacillus subtilis* as described above were prepared as described below to produce crystals:

1. The ultra-filtrate concentrate was equilibrated to the desired starting temperature (see Table 1).
2. 5% NaCl was added with gentle mixing.
3. For all experiments, the solution is maintained at the noted temperature except for experiment 2, in which a sample was drawn from experiment #1 after four hours and incubated at 22° C. with gentle mixing.
4. Crystal habits were observed over time by examining the sample under a microscope.
5. The activity that remained in the supernatant over time was assayed and the percent crystallization was calculated.

TABLE 1

| | Temperature Profile | % Crystallization | Crystal Morphology |
|---|---|---|---|
| Experiment 1 | 15° C. for 4 hour | 70–80% at 22 hr | See FIG. 3 |
| Experiment 2* | 15° C. for 4 hours, shift to 22° C. | 90+% at 22 hr | See FIG. 4 |

TABLE 1-continued

| | Temperature Profile | % Crystallization | Crystal Morphology |
|---|---|---|---|
| Experiment 3 | 22° C. | 95% complete between 4.75 to 19.5 hr | See FIG. 1 |
| Experiment 4 | 30° C. | 95% complete between 4.75 to 19.5 hr | See FIG. 2 |

In experiment 2, without wishing to be bound by theory, it appears that the low temperature at the beginning brought about the square shape nuclei but once placed at a higher temperature, some crystals grow according to a rod shape. The combination of these have resulted in rectangular plates and some rods.

Various other examples and modifications of the foregoing description and examples will be apparent to a person skilled in the art after reading the disclosure without departing from the spirit and scope of the invention, and it is intended that all such examples of modifications be included within the scope of the appended claims. All publications and patents referenced herein are hereby incorporated by reference in their entirety.

What is claimed:

1. A method for crystallization of enzymes to obtain enzyme crystals with a desired crystal morphology, the method comprising:
   a). preparing an aqueous solution containing one or more enzymes;
   b). adding a salt to the aqueous solution to form an enzyme/salt solution;
   c). placing the enzyme/salt solution at a temperature of between about 4° C. and 20° C. for no more than about 5 hours to allow crystals exhibiting the desired morphology to begin to form;
   d). shifting the temperature of the solution to between about 22° C. and 60° C. for no more than about 20 hours to allow continued formation of crystals.

2. The method of claim 1 wherein the one or more enzymes of the recovered crystals have at least about 80% original activity remaining.

3. The method of claim 1, wherein the aqueous solution is derived from one or more fermentation broths.

4. The method of claim 3, wherein cellular debris present in the fermentation broth is removed therefrom to produce a cell-free filtrate.

5. The method of claim 3, wherein the aqueous solution is concentrated prior to crystallization.

6. The method of claim 3, wherein the aqueous solution is an ultra-filtrate concentrate of the fermentation broth.

7. The method of claim 1, wherein the one or more enzymes comprises a hydrolase.

8. The method of claim 1, wherein the one or more enzymes comprises an enzyme selected from the group consisting of protease, amylase, lipase, cellulase, oxidase, transferase, dehydratase, reductase, hemicellulase, and isomerase.

9. The method of claim 1, wherein the desired crystal morphology is selected from square, rectangle, and hexagonal.

10. The method of claim 9, wherein at least a portion of the crystals are square plates.

11. The method of claim 1 wherein the salt is sodium chloride.

12. A method for crystallization of protease to obtain crystals with a desired crystal morphology, the method comprising:
   a). preparing an aqueous solution comprising protease;
   b). adding a salt to the aqueous solution to form a protease/salt solution;
   c). placing the protease/salt solution at a temperature of between about 4° C. and 20° C. for no more than about 5 hours to allow crystals exhibiting the desired morphology to begin to form;
   d). shifting the temperature of the solution to between about 22° C. and 60° C. for no more than about 20 hours to allow continued formation of crystals exhibiting the desired morphology.

13. The method of claim 12 wherein the salt is sodium chloride.

14. The method of claim 12 wherein the protease is an ultra-filtrate concentrate of a fermentation broth.

* * * * *